(12) United States Patent
Festy et al.

(10) Patent No.: US 10,609,291 B2
(45) Date of Patent: Mar. 31, 2020

(54) AUTOMATIC EXPOSURE CONTROL FOR ENDOSCOPIC IMAGING

(71) Applicant: KING'S COLLEGE LONDON, London (GB)

(72) Inventors: Frederic Festy, London (GB); Richard Cook, London (GB); Timothy Watson, London (GB)

(73) Assignee: King's College London, London (GB)

( * ) Notice: Subject to any disclaimer, the term of this patent is extended or adjusted under 35 U.S.C. 154(b) by 402 days.

(21) Appl. No.: 15/328,715

(22) PCT Filed: Jul. 17, 2015

(86) PCT No.: PCT/GB2015/052072
§ 371 (c)(1),
(2) Date: Jan. 24, 2017

(87) PCT Pub. No.: WO2016/012761
PCT Pub. Date: Jan. 28, 2016

(65) Prior Publication Data
US 2017/0214835 A1 Jul. 27, 2017

(30) Foreign Application Priority Data
Jul. 24, 2014 (GB) .................................. 1413109.8

(51) Int. Cl.
*H04N 5/235* (2006.01)
*H04N 5/353* (2011.01)
(Continued)

(52) U.S. Cl.
CPC ....... *H04N 5/2351* (2013.01); *A61B 1/00006* (2013.01); *A61B 1/00009* (2013.01);
(Continued)

(58) Field of Classification Search
CPC .... H04N 5/2351; H04N 5/2256; H04N 5/353; H04N 5/2353; G02B 23/20; A61B 1/045; A61B 1/04
See application file for complete search history.

(56) References Cited

U.S. PATENT DOCUMENTS

| 6,503,195 B1 | 1/2003 | Keller et al. |
| 6,906,745 B1 | 6/2005 | Fossum et al. |

(Continued)

FOREIGN PATENT DOCUMENTS

| EP | 2 547 093 A1 | 1/2013 |
| WO | WO 2009/029810 | 3/2009 |

OTHER PUBLICATIONS

International Application No. PCT/GB2015/052072 International Search Report and Written Opinion dated Oct. 5, 2015 (13 pages).
(Continued)

*Primary Examiner* — Nasser M Goodarzi
*Assistant Examiner* — Patrick A Ryan
(74) *Attorney, Agent, or Firm* — Keller Jolley Preece

(57) ABSTRACT

An endoscopic apparatus and method to capture an image of in-vivo tissue with automatic exposure control. For example, the method includes capturing image data on an image sensor and analyzing an indication of brightness of each pixel to determine whether the captured image data is saturated. When the image data is saturated, the method includes reducing the exposure period by a first increment, and repeating the capturing and analyzing steps until the captured image data is not saturated. When the captured image data is not saturated, in some embodiments, the method includes analyzing the indication of brightness of each pixel compared to a threshold indicative of use of a proportion of an available dynamic range of the image sensor, and when it is determined that the threshold has not been reached, increasing the exposure period by a second
(Continued)

increment that has a magnitude relative to the first increment.

12 Claims, 1 Drawing Sheet

(51) Int. Cl.
    *A61B 1/06*     (2006.01)
    *A61B 1/00*     (2006.01)
    *A61B 1/05*     (2006.01)
    *G02B 23/20*     (2006.01)
    *A61B 1/045*     (2006.01)
    *G02B 23/24*     (2006.01)
    *H04N 5/225*     (2006.01)

(52) U.S. Cl.
    CPC ............... *A61B 1/045* (2013.01); *A61B 1/05* (2013.01); *A61B 1/0669* (2013.01); *G02B 23/20* (2013.01); *G02B 23/2484* (2013.01); *H04N 5/2256* (2013.01); *H04N 5/2353* (2013.01); *H04N 5/353* (2013.01); *H04N 2005/2255* (2013.01)

(56) References Cited

U.S. PATENT DOCUMENTS

| | | | |
|---|---|---|---|
| 2003/0086010 A1* | 5/2003 | Luo | H04N 5/2351 348/297 |
| 2003/0098922 A1* | 5/2003 | Barkan | H04N 5/2351 348/362 |
| 2009/0086046 A1* | 4/2009 | Reilly | H04N 5/2353 348/222.1 |
| 2009/0207182 A1* | 8/2009 | Takada | G09G 3/3406 345/589 |
| 2010/0315514 A1* | 12/2010 | Uchida | H04N 5/23212 348/187 |
| 2011/0085062 A1 | 4/2011 | Rhodes | |
| 2013/0243283 A1 | 9/2013 | Kotchou et al. | |
| 2014/0171738 A1* | 6/2014 | Kagaya | A61B 1/051 600/109 |

OTHER PUBLICATIONS

Application No. GB1413109.8 Search Report under Section 17 dated Sep. 17, 2014 (1 page).

\* cited by examiner

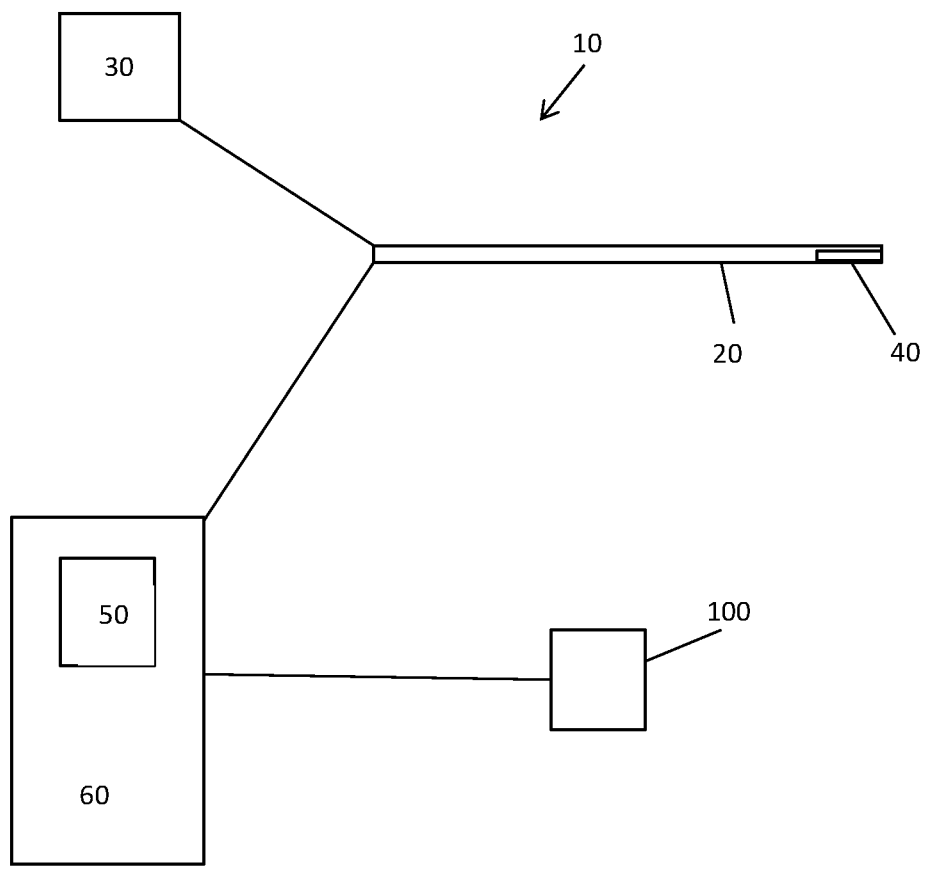

AUTOMATIC EXPOSURE CONTROL FOR ENDOSCOPIC IMAGING

FIELD OF THE INVENTION

The present invention relates to endoscopic apparatus configured to capture an image of in-vivo tissue and configured to perform automatic exposure control and a method for automatic exposure control of an endoscopic apparatus configured to capture an image of in-vivo tissue.

BACKGROUND

Endoscopy is known. Endoscopic apparatus typically comprises a device which can be inserted into, for example, a body or organ of a body, in order to collect one or more "images" of the inside of the body or organ. The "image" may comprise a dataset representative of the inside of the body or organ. That dataset may be recorded and/or may be displayed as an visual representation of the inside of the body or organ on visual display equipment, for example, a video or computer screen.

An endoscope typically comprises: an elongate housing in the form of a rigid or flexible tube; a light source for illuminating tissue of interest; one or more optical elements forming a camera to image tissue of interest; and an image display element, for example, an eyepiece or video screen. The camera and image display are often digital and suitable logic is provided to control operation of the camera to secure useful images.

Since an endoscope is designed for insertion into a body or organ of a body, elements forming the endoscope typically have small dimensions. Often the field of view of an endoscope is restricted.

Collection of images of tissue by an endoscope may be subject to various difficulties. Those difficulties may be related to tissue of interest. It is an object of the present invention to address one or more of those difficulties.

SUMMARY

Accordingly, a first aspect provides a method for automatic exposure control of an endoscopic apparatus configured to capture an image of in-vivo tissue; the method comprising: (i) capturing image data on an image sensor using an exposure period, the image data comprising: an indication of brightness captured by each pixel of the image sensor; (ii) analysing the indication of brightness of each pixel to determine whether the captured image data is saturated; and when it is determined that the captured image data is saturated: (iii) reducing the exposure period by a first increment, and repeating steps (i) and (ii) until it is determined that the captured image data is not saturated; when it is determined that the captured image data is not saturated: (iv) analysing said indication of brightness of each pixel to determine whether a threshold indicative of use of a selected proportion of an available dynamic range of the image sensor has been reached; and when it is determined that the threshold has not been reached: increasing the exposure period by a second increment; wherein the first increment has a magnitude at least three times that of the second increment.

The first aspect recognises that when using an endoscope, disparity of reflectivity of tissue across the small field of view can result in capture of images which are subject to significant saturation. In particular, such disparity in reflectivity between tissue, for example, between gingiva and lip tissue within a human mouth, can cause capture of unusable clinical image data. The first aspect recognises that in order to try to ensure capture of useful images which can provide image data which can be analysed post-acquisition to provide quantitative clinically useful results, as well as providing images which can be viewed by a user in real-time on capture, a user may need to take steps to alter the operational parameters under which image capture occurs. In general, in order to capture a useful image, a user may alter, for example: illumination, gain and/or exposure parameters to try to ensure useful data is collected to form an image of tissue. Relative movement between a subject, endoscope and/or the tissue of interest can cause rapid reflectivity and absorption changes within the field of view, so alteration of parameters may need to take into account the rapidly and unpredictably changing imaging conditions.

Typically a fixed light source, having a substantially fixed intensity is used for endoscopy. Alteration of the intensity of such a light source is unlikely to occur within timescales required to support a video stream of images, which may be required in many clinical applications, particularly in the event of movement of tissue of interest.

Alteration of gain of captured images can be problematic. As gain increases, noise increases. In particular, analogue to digital conversion (ADC), which occurs as part of the image capture process as captured photons at each array element of a photon capture device are quantified and converted to a representative number, is not a linear process across the whole gain range. It will also be understood that gain error adds to that non-linearity and that applying gain to collected data may not keep signal to noise ratio constant. As a result, if it is necessary to perform comparative analysis between collected images, those comparisons may be subject to error. Although it is possible to apply an image capture method according to which illumination is high and gain applied is low, that route may cause unnecessary or undesirable heating of tissue under examination. Furthermore, the first aspect appreciates that from the point of view of noise, it may be advantageous to keep the gain of an image capture method substantially fixed.

Alteration of exposure time can assist with image capture. Alteration of exposure time is more linear in relation to signal to noise ratio than alteration of gain. The first aspect recognises that although reduction of exposure time can result in a "darker" image, the signal information from which an image may be formed or upon which comparisons may be based remains meaningful.

The first aspect relates to a powerful and reliable endoscopic auto-exposure routine. Use of an auto-exposure routine in accordance with the first aspect can assist a user by negating the need to manually change exposure time (ET) and/or gain of a camera of an endoscope, which can be cumbersome and time consuming.

Automatic exposure routines are known. However, an auto-exposure routine in accordance with the first aspect recognises that when it comes to clinical endoscopy it can be more appropriate to capture an image which is "dark" but in which the integrity of the captured data is maintained. The first aspect recognises that avoiding saturation in an endoscopic image may be useful and that capture of image data which could be described as relating to an underexposed image is likely to still be useful, though it may not result in an image which is as immediately pleasing to the eye.

Accordingly, the first aspect may provide a method for automatic exposure control of an endoscopic apparatus configured to capture an image of in-vivo tissue. As described previously, the endoscopic apparatus may comprise: an elongate housing in the form of a rigid or flexible tube, a light source for illuminating tissue of interest, one or more optical elements forming a camera to image tissue of interest, an image display element, for example, an eyepiece or video screen. The camera and image display are often digital and suitable logic is provided to control operation of the camera to secure useful images. The endoscopic apparatus may, for example, be configured to act as a vascularoscope, imaging blood vessels and/or blood flow within tissue of interest.

The method may comprise: capturing image data on an image sensor using an exposure period. The image sensor may comprise a CCD array. The exposure period may comprise an initial or starting exposure period for capture of an initial set of image data.

The image data may comprise: an indication of brightness captured by each pixel of the image sensor. The indication of brightness may comprise an indication of a number of photons collected at each element of the CCD array.

The method may comprise: analysing the indication of brightness of each pixel to determine whether the captured image data is saturated. A threshold or indication of "saturation" of image data may be selected in accordance with the type of image being captured by the endoscope. In particular, saturation may depend upon whether the image being collected is of a tissue based on reflection or absorption of illumination or fluorescence of a tissue being subjected to illumination.

According to the first aspect, if it is determined that the captured image data is saturated, the method may comprise: reducing the exposure period by a first increment, and repeating capture of image data and analysis of captured image data in relation to saturation until it is determined that the captured image data is not saturated. Accordingly, the method of the first aspect recognises that it can be important to reduce exposure time as soon as a selected saturation level of captured image data is reached. The saturation level can be selected, for example, such that the exposure time is reduced as soon as the data collected by the image sensor becomes detrimental to potential analysis which may be required in relation to the image data. In the case of vascular imaging, for example, the saturation level at which exposure time is decreased may be chosen as soon as the image data is such that it is unlikely to be useful in relation to analysis of vascular pattern, blood cell counting and/or blood flow analysis.

According to the first aspect, if it is determined that the captured image data is not saturated, then the method may comprise: analysing the indication of brightness of each pixel to determine whether a threshold indicative of use of a selected proportion of an available dynamic range of the image sensor has been reached. Accordingly, the auto-exposure method of the first aspect recognises that in order to obtain useful image data for analysis, it can be beneficial to try to ensure that the dynamic range of the image sensor is substantially fully exploited, thereby ensuring that the image data collected is useful for comparative analysis, if required.

A method according to the first aspect may be performed such that if it is determined that the threshold has not been reached: steps are taken to increase the exposure period by a second increment. The increase in exposure time may be performed slowly, relative to the decrease in exposure time taken to avoid saturation in collected or captured image data.

According to the auto-exposure method of the first aspect, the first increment (decrease in exposure time to avoid saturation conditions) may have a magnitude at least three times that of the second increment (increase in exposure time to ensure a dynamic range of the image sensor is utilised). Accordingly, an auto-exposure routine in accordance with the first aspect recognises that captured image data in which the dynamic range of an image sensor is not optimally utilised may be of use, whereas a saturated image may be of no use. Accordingly, asymmetric steps in exposure time are implemented, such that highly evasive action is taken to address image data which appears to be saturated, and smaller changes are then implemented to try to utilise available sensor detection range. It will be appreciated that by implementing a method in accordance with described aspects and embodiments, an auto exposure route in which a fast and dramatic exposure period reduction is implemented if saturation is detected, followed by an increase in exposure period which is slow enough to avoid oscillation of the algorithm and fast enough for a user not to experience unacceptable lag. According to embodiments, the ratio between the up and down factor may be between 1:3 and 1:10. It will, or course, be appreciated that one or both of the increments may comprise a fixed change and be independent of a currently applied exposure period, or may comprise a percentage increase or decrease in exposure period, and therefore be dependent upon the initial exposure value.

In one embodiment, reducing the exposure period by a first increment comprises: reducing the exposure period by between 33% and 75%. In one embodiment, reducing the exposure period by a first increment comprises: reducing the exposure period by between 40% and 60%. In one embodiment, reducing the exposure period by a first increment comprises: reducing the exposure period by around 50%. In one embodiment, reducing the exposure period by a first increment comprises: reducing the exposure period by 50%. Accordingly, halving the exposure period can help to ensure that captured image data is not saturated. Such a change to exposure time may also help to ensure that calls to exposure time adjustment logic are minimal, since repeated calls to adjust exposure period can significantly slow image sensor acquisition speed. This is further guaranteed by appropriate selection of saturation threshold and range intensity threshold, as described in more detail below. If the range intensity threshold is sufficiently different to the saturation threshold and changes are made to increase the exposure time slowly if the intensity range threshold is not met, then unnecessary frequent changes to exposure period can be mitigated.

In one embodiment, increasing the exposure period by a second increment comprises: increasing the exposure period by between 1% and 20%. In one embodiment, the exposure period is increased by between 10% and 25%. In one embodiment, the exposure period is increased by between 5% and 20%. In one embodiment, the exposure period is increased by around 10%. In one embodiment, the exposure period is increased by 10%. Accordingly, such a relatively small increase allows for a slow increase in exposure time period and is selected such that feedback oscillation, which can create a flashing video output when sequential captured images are shown on a video screen, can be mitigated.

In one embodiment, determining whether the captured image data is saturated comprises: selecting a brightest proportion of the indication of brightness captured by each pixel of the image sensor; determining an average intensity of the selected brightest proportion and comparing the average intensity to a saturation threshold. Accordingly, an indication of the number of saturated pixels can be obtained. In other words, if the brightness value recorded by each pixel is ordered according to brightness, and, for example, the highest (brightest) 25% of those pixels have their brightness value averaged, it is possible to obtain an indication of the brightness of an image. Such an approach allows the brightness of an image to be related to likelihood of saturation in the captured image data.

In one embodiment, the brightest proportion selection is dependent upon image size. Accordingly, the proportion of pixels used to offer an indication of image data saturation may depend upon image size, or, in other words, the total number of indications of pixel brightness which form the image data. The larger the number of pixels, the smaller the number of pixels which may be required to offer a representative indication of image data saturation.

In one embodiment, the brightest proportion selection comprises: between 0.05% and 2% of the total number of pixels of the image sensor. In one embodiment, the brightest proportion selection comprises: around 0.5% of the total number of pixels of the image sensor. In one embodiment, the brightest proportion selection comprises: around 0.5% of the total number of pixels of the image sensor. Use of an average of a proportion of the pixels rather than simply looking at the highest recorded value helps to avoid inherent fluctuations associated with a single "highest" value. Since a relatively large decrease in exposure period is implemented if it is determined that a saturation threshold is reached, it is appropriate to try to ensure that the decrease is only taken when it is appropriate to do so. It will be appreciated that the proportion of pixels selected for averaging may be dependent upon the particular type of endoscopic application. For example, in relation to fluorescence images, the proportion may be low, perhaps in the region of 0.01 to 0.2%, since it is the "bright" part of the image data which would contain the data of interest. According to such an endoscopic application an embodiment may be implemented in which the proportion of pixels considered for averaging purposes could be "object" pixels rather than total number of sensor pixels.

In one embodiment, the indication of brightness captured by each pixel of the image sensor comprises a numerical value between zero and a maximum recordable brightness and wherein the saturation threshold comprises the maximum recordable brightness. For example, an image sensor may comprise a 12 bit image sensor, such that the sensitivity, or granularity, of the indication of brightness collected by each pixel may be any value between 0 and 4095. If shown on a monochrome or grey scale image reproduction device, those recorded values forming the image data may be mapped to, for example, a 256 grey scale, which may cause an associated reduction in granularity of the collected image data. An appropriate saturation threshold may depend upon whether saturation threshold calculations are based upon raw brightness data from the image sensor, or image data as converted for reproduction on a video screen. In any case, the saturation threshold may be selected to be the maximum recordable value. If the average indication of brightness value in relation to the selected proportion of pixels, or data points, is the maximum, then all of the data points in the subset being considered are likely to be recorded at the maximum possible value, meaning any information regarding variation of brightness in that subset is "lost" since the image sensor cannot record a higher brightness than the maximum. It will be appreciated that it is likely that the maximum possible value recordable is an appropriate saturation threshold. This means, for example, in the case of a 12 bit CCD, if the brightest 0.5% of pixels are averaged and a value of 4095 is obtained, then at least 0.5% of the pixels are saturated and "unusable" data. Although a lower saturation threshold may be used, it may be more appropriate, in some embodiments, to change the proportion of brightest pixels which are averaged to give an indication of saturation.

In one embodiment, analysing the indication of brightness of each pixel to determine whether a threshold indicative of use of a selected proportion of an available range of the image sensor has been reached comprises: selecting a brightest proportion of the indication of brightness captured by each pixel of the image sensor; determining an average intensity of the selected brightest proportion and comparing the average intensity to a range intensity threshold. Accordingly, If the average indication of brightness value in relation to the selected proportion of pixels, or data points, is found to be at a value indicative of use of the full dynamic range of the sensor, then it is likely that the data points forming the image data a spread across the available range and that information about a tissue of interest is available. One means to determine whether the full dynamic range of the sensor is being used is to consider a proportion of the "brightest" data points and average those data points. If the average of those data points is around a pre-determined threshold value or within a preselected range indicative of adequate or optimised sensor range usage, it is likely that the image data collected comprises data which uses available sensitivity available and that maximum possible information is being collected about the tissue of interest in that particular image capture.

In one embodiment, the indication of brightness captured by each pixel of the image sensor comprises a numerical value between zero and a maximum recordable brightness and wherein the range intensity threshold comprises a value approximately 75% of the maximum recordable brightness. It will be appreciated that the threshold may take into account an optimised range rather than a full range of intensities which may be recorded by a sensor. It will be appreciated, for example, that if a 12 bit CCD sensor device is available (0 to 4095 recordable values) and that image data captured using that sensor only has values between 0 and 1024, then it would possibly be more appropriate to be using a 10 bit CCD as a sensor. Embodiments operate to try to ensure that the full number of bits available is adequately utilised. If N is the number of bits available then optimised use of available bits may be given by between $2^{N-1}$ to $2^N-1$. For example, if N=12 then an optimised range may be between 2048 and 4095 (since 2048 is unattainable by an 11 bit CCD). The maximum available using an 11 bit CCD would be $2^{11}-1=2047$. It will also be appreciated that if optimised use of available CCD capability is of less concern, the optimised intensity range may be given by between $2^{N-2}$ to $2^N-1$.

In one embodiment, the "brightest proportion" of pixels used to calculate an indication of available range is the same as the "brightest proportion" of pixels used to generate an indication of saturation. Use of the same proportion of pixels can help to ensure computational processing is minimised and that there is no need to perform additional calculations. In relation to range utilisation a fluctuating value, as a result of a low number of pixels being averaged, is off less significance since the increase in exposure time as a result of the intensity threshold not being met is small in comparison to the cut in exposure time invoked in response to an indication of saturation exceeding the saturation threshold.

In one embodiment, capturing image data on an image sensor using an exposure period occurs at a selected frame capture rate and the exposure period is less than a time period between successive frame captures. Accordingly, it will be appreciated that the auto-exposure routine may be used in relation to a video stream. An auto exposure routine in accordance with the first aspect can be used in relation to successive image captures within such a video stream, subject to a maximum possible exposure period being less than the time period between successive frame captures as required by the video stream.

In one embodiment, the method comprises: stabilising a series of displayed images resulting from the captured image data by: adjusting the captured image data such that: a selected proportion of the indication of brightness captured by each pixel of the image sensor is allocated a minimum possible indication value and a selected proportion of the indication of brightness captured by each pixel of the image sensor is allocated a maximum possible indication value. Accordingly, overall image brightness and contrast can be stabilised, such that a resulting video stream is visually appealing.

A second aspect provides a computer program product operable, when executed on a computer, to perform the method of the first aspect.

A third aspect provides endoscopic apparatus configured to capture an image of in-vivo tissue and configured to perform automatic exposure control; the apparatus comprising: image capture logic configured to capture image data on an image sensor using an exposure period, the image data comprising: an indication of brightness captured by each pixel of the image sensor; analysis logic operable to analyse the indication of brightness of each pixel to determine whether the captured image data is saturated; and adjustment logic configured, when it is determined that the captured image data is saturated: to reduce the exposure period by a first increment, and repeat the capture and adjustment steps until it is determined that the captured image data is not saturated; and when it is determined that the captured image data is not saturated: the analysis logic being further configured to analyse the indication of brightness of each pixel to determine whether a threshold indicative of use of a selected proportion of an available dynamic range of the image sensor has been reached; and when it is determined that the threshold has not been reached: the adjustment logic being further configured to increase the exposure period by a second increment; wherein the first increment has a magnitude at least three times that of the second increment.

In one embodiment, the adjustment logic is operable to reduce the exposure period by by between 33% and 75%. In one embodiment, the adjustment logic is operable to reduce the exposure period by between 40% and 60%. In one embodiment, the adjustment logic is operable to reduce the exposure period by around 50%. In one embodiment, the adjustment logic is operable to reduce the exposure period by 50%.

In one embodiment, the adjustment logic is operable to increase the exposure period by between 1% and 20%. In one embodiment, the adjustment logic is operable to increase the exposure period by between 10% and 25%. In one embodiment, the adjustment logic is operable to increase the exposure period by between 5% and 20%. In one embodiment, the adjustment logic is operable to increase the exposure period by around 10%. In one embodiment, the adjustment logic is operable to increase the exposure period by 10%.

In one embodiment, the analysis logic is operable to determine whether the captured image data is saturated by: selecting a brightest proportion of the indication of brightness captured by each pixel of the image sensor; determining an average intensity of the selected brightest proportion and comparing the average intensity to a saturation threshold.

In one embodiment, the brightest proportion selection is dependent upon image size.

In one embodiment, the brightest proportion selection comprises: between 0.05 and 2% of the total number of pixels of the image sensor. In one embodiment, the brightest proportion selection comprises: 0.5% of the total number of pixels of the image sensor.

In one embodiment, the indication of brightness captured by each pixel of the image sensor comprises a numerical value between zero and a maximum recordable brightness and wherein the saturation threshold comprises the maximum recordable brightness.

In one embodiment, the analysis logic is operable to analyse the indication of brightness of each pixel to determine whether a threshold indicative of use of a selected proportion of an available range of the image sensor has been reached by selecting a brightest proportion of the indication of brightness captured by each pixel of the image sensor; determining an average intensity of the selected brightest proportion and comparing the average intensity to a range intensity threshold.

In one embodiment, the indication of brightness captured by each pixel of the image sensor comprises a numerical value between zero and a maximum recordable brightness and wherein the range intensity threshold comprises a value approximately 75% of the maximum recordable brightness.

In one embodiment, capturing image data on an image sensor using an exposure period occurs at a selected frame capture rate and the exposure period is less than a time period between successive frame captures.

Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

BRIEF DESCRIPTION OF THE DRAWINGS

Embodiments of the present invention will now be described further, with reference to the accompanying drawings, in which:

FIG. 1 illustrates schematically main components of an endoscopic apparatus of one arrangement.

DESCRIPTION OF THE EMBODIMENTS

FIG. 1 illustrates schematically main components of an endoscopic apparatus of one arrangement. The endoscopic apparatus 10 shown comprises a device which can be inserted into, for example, a body or organ of a body, in order to collect one or more "images" of the inside of the body or organ. The "image" may comprise a dataset representative of the inside of the body or organ. That dataset may be recorded and/or may be displayed as a visual representation of the inside of the body or organ on visual display equipment, for example, a video or computer screen 100.

An endoscope typically comprises: an elongate housing 20 in the form of a rigid or flexible tube, a light source 30 coupled to the elongate housing and arranged to illuminate tissue of interest, one or more optical elements forming a camera 40 to image tissue of interest, an image display element, for example, an eyepiece or video screen 100. The camera and image display are often digital and suitable control logic 50 is provided to control operation of the camera 40 to secure useful images of the tissue of interest. The camera control logic 50 is provided within the endoscope control unit 60.

Since an endoscope is designed for insertion into a body or organ of a body, elements forming the endoscope typically have small dimensions. Often the field of view of an endoscope is restricted.

One arrangement of endoscopic apparatus 10 can be configured to capture an image of in-vivo tissue and the camera control logic 50 is configured to perform automatic exposure control in relation to image data being collected by the camera 40 forming part of the endoscopic apparatus 10. The camera control logic provided comprises: image capture logic configured to capture image data on an image sensor using an exposure period, that image data comprising: an indication of brightness captured by each pixel of said image sensor; analysis logic operable to analyse the indication of brightness of each pixel to determine whether the captured image data is saturated; and adjustment logic configured, when it is determined that the captured image data is saturated: to reduce said exposure period by a first increment, and repeat the capture and adjustment steps until it is determined that the captured image data is not saturated; and when it is determined that the captured image data is not saturated the analysis logic is further configured to analyse the indication of brightness of each pixel to determine whether a threshold indicative of use of a selected proportion of an available dynamic range of the image sensor has been reached; and when it is determined that the threshold has not been reached: the adjustment logic being further configured to increase the exposure period by a second increment; wherein the first increment has a magnitude at least three times that of the second increment.

According to one method of operation, the auto-exposure routine is implemented with parameters suited to endoscopic vascular imaging. In particular: an endoscope may be configured to capture image data using a first exposure period. The captured image data comprises a data set relating to brightness captured by each element of a CCD array. The camera control logic is operable to calculate the number of saturated pixels in the captured image data. If the number of saturated pixels exceeds a threshold, then exposure time is altered. The threshold, according to one implementation, is related to the total set of data points in the image data and may, for example, comprise 0.5% of the total number of data points/pixels.

If the selected saturation threshold is reached, then the camera control logic is operable to divide the exposure period being used by the camera by two.

In order to avoid a change in overall image brightness and contrast between consecutive images in a stream of images as a result of such a sudden change to exposure time, the endoscopic control unit 60 may be operable to ensure each frame is displayed by the display unit 100 with a selected number of saturated pixels in both extreme black and extreme white. In one implementation, the number of saturated pixels in the display is matched to the maximum allowed number of saturated data points (pixels) in the image data (in the given example, 0.5%). As a result, the reduction in exposure time is substantially unnoticeable to the human eye looking at the video screen 100, albeit that the change to exposure period is likely to have provided a slight increase in the signal to noise ratio.

If the saturation check reveals that the saturation threshold has not been met, then the average intensity of the brightest 0.5% of pixels (data points) is calculated. If that average lies above a selected threshold indicative of full use of available dynamic range, no action is taken. However, if the average is determined to be less than the threshold indicative of full use of available dynamic range of the image sensor, then steps are taken by the camera control logic to increase exposure period when imaging tissue of interest. In one implementation, in which a 12 bit CCD is provided, the threshold may be selected to be 75% of the full dynamic range, which gives a value of 3072 (0.75×4095). It has been found that using the average intensity of the brightest 0.5% of pixels may allow enhanced stability of the auto exposure algorithm and can enable the removal of "jitter" from poisson noise associated with data capture.

If the average intensity value is found to be below the selected threshold value, the camera control logic is operable to increase the exposure period in relation to image capture by 10%. Such an increment minimises the risk of oscillation between an over and under exposed image, which would be likely to create a flashing video output, detrimental to an end user experience.

Increasing the exposure period by 10% is not likely to be noticed by the end user, since steps are taken to display sequential frames with a substantially identical overall saturation level. The signal to noise ratio can be slowly increased by use of the described process, by a factor of approximately 4.9%.

An auto-exposure routine in accordance with aspects and embodiments described herein can be run at the same speed as the acquisition of image data (for example, 31 frames per second) and the method can be fast enough to allow components of the endoscopic apparatus to respond in an appropriate timescale. Typically less than 10 frames are necessary to implement an appropriate series of changes to exposure period, thus offering an image stabilisation time of approximately 300 ms once saturation is detected.

The implementation described can offer high overall image stability within a video stream, since the exposure period is only altered when the top 0.5% of the data points (pixels) in the image data is above or below selected thresholds. The range over which this average intensity is "allowed" to vary is, in the example given, approximately 25% of the dynamic range of the CCD.

The images being shown to an end user appear to be particularly stable since additional steps can be taken to rescale overall intensity of the image when shown on the video display. However, such rescaling need not be done in relation to image data stored and requiring further quantitative analysis.

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

The invention claimed is:

1. A method for automatic exposure control of an endoscopic apparatus configured to capture an image of in-vivo tissue, comprising:
   capturing image data on an image sensor using an exposure period, the image data comprising: an indication of brightness captured by each pixel of the image sensor;
   analyzing the indication of brightness of each pixel to determine whether the captured image data is saturated, wherein determining whether the captured image data is saturated comprises:

selecting a brightest proportion of the indication of brightness captured by each pixel of the image sensor; and determining an average intensity of the selected brightest proportion and comparing the average intensity to a saturation threshold; and when it is determined that the captured image data is saturated:

reducing the exposure period by a first increment, and repeating the steps of capturing image data and analyzing the indication of brightness of each pixel until it is determined that the captured image data is not saturated;

when it is determined that the captured image data is not saturated:

analyzing the indication of brightness of each pixel to determine whether a threshold indicative of use of a selected proportion of an available dynamic range of the image sensor has been reached; and when it is determined that the threshold has not been reached, increasing said exposure period by a second increment, wherein the first increment has a magnitude at least three times that of the second increment.

2. A method according to claim 1, wherein reducing the exposure period by a first increment comprises reducing the exposure period by between 33% and 75%.

3. A method according to claim 1, wherein increasing the exposure period by a second increment comprises increasing the exposure period by between 1% and 20%.

4. A method according claim 1, wherein the brightest proportion selection is dependent upon image size.

5. A method according to claim 1, wherein the brightest proportion selection comprises between 0.05% and 2% of the total number of pixels of the image sensor.

6. A method according to claim 1, wherein the indication of brightness captured by each pixel of the image sensor comprises a numerical value between zero and a maximum recordable brightness and wherein the saturation threshold comprises the maximum recordable brightness.

7. A method according to claim 1, wherein analyzing the indication of brightness of each pixel to determine whether the threshold indicative of use of the selected proportion of the available range of the image sensor has been reached comprises:

selecting a brightest proportion of the indication of brightness captured by each pixel of the image sensor; and determining an average intensity of the selected brightest proportion and comparing the average intensity to a range intensity threshold.

8. A method according to claim 7, wherein the indication of brightness captured by each pixel of the image sensor comprises a numerical value between zero and a maximum recordable brightness and wherein the range intensity threshold comprises a value approximately 75% of the maximum recordable brightness.

9. A method according to claim 1, wherein capturing image data on the image sensor using the exposure period occurs at a selected frame capture rate and the exposure period is less than a time period between successive frame captures.

10. A method according to claim 1, further comprising stabilizing a series of images resulting from the captured image data by adjusting the captured image data such that a selected proportion of the indication of brightness captured by each pixel of the image sensor is allocated a minimum possible indication value and a selected proportion of the indication of brightness captured by each pixel of said image sensor is allocated a maximum possible indication value.

11. A non-transitory computer readable storage media storing instructions thereon that, when executed by a processor, cause a computer system to:

capture image data on an image sensor using an exposure period, the image data comprising: an indication of brightness captured by each pixel of the image sensor;

analyze the indication of brightness of each pixel to determine whether the captured image data is saturated, wherein determining whether the captured image data is saturated comprises:

selecting a brightest proportion of the indication of brightness captured by each pixel of the image sensor; and determining an average intensity of the selected brightest proportion and comparing the average intensity to a saturation threshold; and when it is determined that the captured image data is saturated:

reduce the exposure period by a first increment, and repeating the steps of capturing image data and analyzing the indication of brightness of each pixel until it is determined that the captured image data is not saturated;

when it is determined that the captured image data is not saturated:

analyze the indication of brightness of each pixel to determine whether a threshold indicative of use of a selected proportion of an available dynamic range of the image sensor has been reached; and when it is determined that the threshold has not been reached, increasing said exposure period by a second increment, wherein the first increment has a magnitude at least three times that of the second increment.

12. An endoscopic apparatus configured to capture an image of in-vivo tissue and configured to perform automatic exposure control, the apparatus comprising:

image capture logic to capture image data on an image sensor using an exposure period, the image data comprising an indication of brightness captured by each pixel of said image sensor;

analysis logic to analyze the indication of brightness of each pixel to determine whether the captured image data is saturated, wherein determining whether the captured image data is saturated comprises:

selecting a brightest proportion of the indication of brightness captured by each pixel of the image sensor; and determining an average intensity of the selected brightest proportion and comparing the average intensity to a saturation threshold; and adjustment logic that:

when it is determined that the captured image data is saturated, reduces the exposure period by a first increment, and repeats the capturing image data and analyzing the indication of brightness steps until it is determined that the captured image data is not saturated;

when it is determined that the captured image data is not saturated, analyzes the indication of brightness of each pixel to determine whether a threshold indicative of use of a selected proportion of an available dynamic range of the image sensor has been reached; and when it is determined that said threshold has not been reached, increasing the exposure period by a second increment, wherein said first increment has a magnitude at least three times that of the second increment.

\* \* \* \* \*